US00RE36138E

United States Patent [19]

Suzuki et al.

[11] E Patent Number: Re. 36,138

[45] Reissued Date of Patent: Mar. 9, 1999

[54] PERCUTANEOUS ABSORPTION PROMOTER, A TAPE PLASTER AND A METHOD OF PROMOTING PERCUTANEOUS ABSORPTION

[75] Inventors: Eiji Suzuki; Hideaki Okabe, both of Urawa; Takanori Saito, Misato, all of Japan

[73] Assignee: Lintec Corporation, Tokyo, Japan

[21] Appl. No.: 854,136

[22] Filed: May 8, 1997

Related U.S. Patent Documents

Reissue of:

[64] Patent No.: 5,413,794
Issued: May 9, 1995
Appl. No.: 937,783
Filed: Sep. 1, 1992

[30] Foreign Application Priority Data

Jan. 24, 1992 [JP] Japan ..... 4-034274

[51] Int. Cl.[6] ..... A61F 13/00

[52] U.S. Cl. ..... 424/449; 424/448; 514/946; 514/947

[58] Field of Search ..... 424/448, 449; 514/946, 947

[56] References Cited

U.S. PATENT DOCUMENTS

| | | | |
|---|---|---|---|
| 3,969,087 | 7/1976 | Saito et al. | 44/270 |
| 4,732,892 | 3/1988 | Sarpotdar et al. | 514/178 |
| 4,789,667 | 12/1988 | Makino | 514/161 |
| 4,808,414 | 2/1989 | Peck | 424/449 |
| 4,963,556 | 10/1990 | Alexander | 514/262 |
| 4,980,378 | 12/1990 | Wong et al. | 514/785 |
| 5,059,628 | 10/1991 | Tsuda | 514/784 |
| 5,082,866 | 1/1992 | Wong | 514/785 |

FOREIGN PATENT DOCUMENTS 2281162 3/1976 France .

OTHER PUBLICATIONS

Patent Abstracts of Japan, vol. 011, No. 063, Feb. 26, 1987.
Patent Abstracts of Japan, vol. 9, No. 324, Dec. 19, 1985.

*Primary Examiner*—Thurman K. Page
*Assistant Examiner*—D. Gabrielle Brouillette
*Attorney, Agent, or Firm*—Millen, White, Zelano, & Branigan, P.C.

[57] ABSTRACT

A percutaneous absorption promoter comprises a derivative of amino acid in which the amino group has or does not have an acyl substituent or a hydrocarbon substituent, the carboxylic group has a hydrocarbon substituent and the part between the amino group and the carboxylic group has a specified structure. A tape plaster comprises the percutaneous absorption promoter described above. The method utilizes the the percutaneous absorption promoter described above. The percutaneous promoter of the invention has excellent ability of promoting the percutaneous absorption of pharmacologically active substances and excellent safety simultaneously, capable of delivering the desired pharmacologically active substances rapidly to the location of treatment or to all parts of the body through the circulating system and effective for curing various kinds of disease. The tape plaster comprising it and the method of promoting percutaneous absorption by utilizing it have the same advantages.

22 Claims, No Drawings

PERCUTANEOUS ABSORPTION PROMOTER, A TAPE PLASTER AND A METHOD OF PROMOTING PERCUTANEOUS ABSORPTION

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a novel percutaneous absorption promoter. More particularly, the present invention relates to a percutaneous absorption promoter, having excellent ability of promoting percutaneous absorption of a pharmacologically active substance and excellent safety simultaneously, capable of delivering the desired pharmacologically active substance rapidly to the location of treatment or to all parts of the body through the circulating system and effective for curing various kinds of disease. The present invention relates also to a novel tape plaster comprising the percutaneous absorption promoter therefore and a novel method of promoting percutaneous absorption by utilizing it.

2. Description of the Prior Art

During the recent progress of medical treatment, transdermal therapeutic systems therefore (TTS) have been developed to absorb percutaneously and deliver desired pharmacologically active substances to all parts of the body and thus to maintain the curing effect for a prolonged time. For example, transdermal therapeutic systems utilizing nitroglycerol or isosorbide dinitrate for curing angina pectoris, those containing clonidine for curing hypertonia and those containing estradiol for curing climacteric difficulties have actually been utilized.

However, even though these transdermal therapeutic systems show many advantages such as evasion of metabolism of the pharmacologically active substances at intestine and liver, reduction of side reactions and increased retention of the pharmacological effect, they have a problem that, because skin essentially has the barrier function against invasion of foreign substances, only limited kinds of pharmacologically active substances can attain the concentration of the substances in blood high enough to show the pharmacological effect and the pharmacologically active substances which can be utilized for the transdermal therapeutic systems are naturally very limited.

Various methods have been tried to improve the percutaneous absorption of pharmacologically active substances. For example, pharmacologically active substances were modified to form prodrugs and complexes. Ionic pharmacologically active substances were utilized with use of iontophoresis. These methods have a problem that the actual administration requires detailed studies on the individual pharmacologically active substance and a long period of time and a large amount of investment are inevitably required. On the other hand, percutaneous absorption promoters which increase percutaneous absorption of pharmacologically active substances by decreasing the barrier property of skin have been actively developed. It is expected by using these percutaneous absorption promoters that various kinds of pharmacologically active substances can be utilized without much limitations.

As the percutaneous absorption promoters, the following compounds, for example, have been utilized: polar solvents, such as dimethylsulfoxide, decylmethylsulfoxide, dimethylformamide and dimethylacetamide; cycloalkanes, such as azacycloheptan-2-one and 1-dodecylazacycloheptan-2-one; esters of carboxylic acids and alcohols, such as isopropyl myristate and isopropyl palmitate; glycols; surface active agents, such as sodium laurylsulfate and sodium dodecylsulfate; and derivatives of fatty acids, pyroglutamic acid and urea which are natural moisturing agents of skin. These absorption promoters have problems that they do not always satisfy both the promotion of the percutaneous absorption and safety, such as safety concerns from toxicity and irritation, and that a long time is required to exhibit the pharmacological activity because of a long lag time in the percutaneous absorption of the pharmacologically active substances.

SUMMARY OF THE INVENTION

The present invention accordingly has an object to provide a percutaneous promoter having excellent ability of promoting the percutaneous absorption of a pharmacologically active substance and excellent safety simultaneously, capable of delivering the desired pharmacologically active substance rapidly to the location of treatment or to all parts of the body through the circulating system and effective for curing various kinds of disease. Another object of the invention is to provide a tape plaster comprising the percutaneous promoter. Still another object of the invention is to provide a method of promoting percutaneous absorption by utilizing it.

Extensive investigations undertaken by the present inventors with the objects described above led therefore to a discovery that a derivative of amino acid having the formula [1] promotes percutaneous absorption of pharmacologically active substances remarkably and has excellent safety simultaneously. The present invention has been completed on the basis of the discovery.

Thus, the percutaneous absorption promoter of the invention comprises a derivative of amino acid having the formula:

$$R^1NH—R^3—COOR^2 \qquad [1]$$

wherein $R^1$ is a hydrogen atom, an acyl group having 1 to 20 carbon atoms or a hydrocarbon group having 1 to 20 carbon atoms, $R^2$ is a hydrogen atom or a hydrocarbon group having 1 to 20 carbon atoms and $R^3$ is

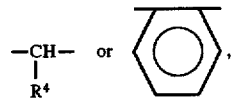

$R^4$ being a hydrogen atom, methyl group, isopropyl group, 2-methylpropyl group or 1-methylpropyl group.

The tape plaster of the invention comprises an adhesive material comprising the percutaneous absorption promoter described above coated on a tape substrate.

The method of promoting percutaneous absorption of the invention comprises promoting percutaneous absorption of a pharmacologically active substance by applying the percutaneous absorption promoter described above in combination with the pharmacologically active substance to a patient locally and percutaneously.

Other and further objects, features and advantages of the invention will appear more fully from the following description.

DETAILED DESCRIPTION OF THE INVENTION

The invention will be described in detail in the following.

The percutaneous absorption promoter of the invention comprises a derivative of an amino acid having the formula [1].

Examples of the acyl group having 1 to 20 carbon atoms as the substituent $R^1$ in the formula [1] are: aliphatic acyl groups, such as formyl group, acetyl group, propanoyl group, butanoyl group, pentanoyl group, octanoyl group, decanoyl group, dodecanoyl group, tetradecanoyl group, palmitoyl group, stearoyl group, oleoyl group, acryloyl group and the like; aromatic acyl groups, such as benzoyl group, toluoyl group, salicyloyl group, cinnamoyl group, naphthoyl group, phthaloyl group, furoyl group, anisoyl group and the like; and the like other groups.

Preferable examples among the acyl groups described above are saturated and unsaturated aliphatic acyl groups having 1 to 20 carbon atoms. More preferable examples among them are saturated and unsaturated linear aliphatic acyl groups having 2 to 16 carbon atoms.

Examples of the hydrocarbon group having 1 to 20 carbon atoms as the substituent $R^1$ in the formula [1]are: alkyl groups, such as methyl group, ethyl group, propyl group, isopropyl group, butyl group, tert-butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, eicosyl group and the like; alkenyl groups, such as ethynyl group, propenyl group, 1-butenyl group, isobutenyl group, 1-pentenyl group, 2-pentenyl group, 3-methyl-1-butenyl group, 1-hexenyl group, tetramethylethynyl group, 1-heptenyl group, 1-octenyl group, 1-nonenyl group, 1-decenyl group, 1-undecenyl group, tridecenyl group, pentadecenyl group, octadecenyl group, eicosenyl group and the like; phenyl groups having one or more alkyl groups or alkenyl groups described above as the substituent; phenylalkyl groups having phenyl group, an alkylphenyl group or an alkenylphenyl group as the substituent to the alkyl group described above, such as benzyl group, phenylethyl group, phenylpropyl group, phenylbutyl group, phenylpentyl group, phenylhexyl group and the like; phenylalkenyl groups having phenyl group, an alkylphenyl group or an alkenylphenyl group as the substituent to the alkenyl group described above.

Preferable examples among the hydrocarbon groups described above are saturated and unsaturated aliphatic hydrocarbons having 1 to 20 carbon atoms. More preferable examples among them are saturated and unsaturated linear aliphatic hydrocarbons having 1 to 20 carbon atoms and most preferable examples among them are saturated and unsaturated linear aliphatic hydrocarbons having 1 to 16 carbon atoms.

Examples of the hydrocarbon group having 1 to 20 carbon atoms as the substituent $R^2$ in the formula [1] are the same as the examples of the hydrocarbon group having 1 to 20 carbon atoms as the substituent $R^1$ in the formula [1]. Preferable examples among them are saturated and unsaturated aliphatic hydrocarbon groups having 1 to 20 carbon atoms and more preferable examples among them are saturated and unsaturated hydrocarbon groups having 1 to 12 carbon atoms.

The substituent $R^4$ in the formula [1] is a hydrogen atom, methyl group, isopropyl group, 2-methylpropyl group or 1-methylpropyl group, and preferably a hydrogen atom.

The derivatives of the amino acids are preferably compounds having the formula [1] wherein $R^1$ is a saturated or unsaturated linear aliphatic acyl group having 2 to 16 carbon atoms and $R^2$ is a saturated or unsaturated linear aliphatic hydrocarbon group having 1 to 4 carbon atoms and, more preferably, compounds having the formula [1] wherein $R^1$ is a saturated or unsaturated linear aliphatic acyl group having 8 to 12 carbon atoms and $R^2$ is a saturated or unsaturated linear aliphatic hydrocarbon group having 1 to 4 carbon atoms.

The derivatives of the amino acids may be any of L-isomers, D-isomers and racemic isomers.

Examples of the derivatives of the amino acids are: ethyl anthranilate, octyl anthranilate, stearyl anthranilate, N-butyloylanthranilic acid, ethyl N-butyloylanthranilate, octyl N-butyloylanthranilate, stearyl N-butyloylanthranilate, N-octanoylanthranilic acid, N-decanoylanthranilic acid, N-dodecanoylanthranilic acid, methyl N-dodecanoylanthranilate, ethyl N-dodecanoylanthranilate, butyl N-dodecanoylanthranilate, octyl N-dodecanoylanthranilate, stearyl N-dodecanoylanthranilate, N-myristoylanthranilic acid, methyl N-myristoylanthranilate, ethyl N-myristoylanthranilate, butyl N-myristoylanthranilate, N-palmitoylanthranilic acid, N-stearoylanthranilic acid, octyl N-stearoylanthranilate, stearyl N-stearoylanthranilate, ethyl ester of glycine, octyl ester of glycine, stearyl ester of glycine, N-butyloylglycine, ethyl ester of N-butyloylglycine, octyl ester of N-butyloylglycine, stearyl ester of N-butyloylglycine, N-octanoylglycine, N-decanoylglycine, N-dodecanoylglycine, methyl ester of N-dodecanoylglycine, ethyl ester of N-dodecanoylglycine, butyl ester of N-dodecanoylglycine, octyl ester of N-dodecanoylglycine, stearyl ester of N-dodecanoylglycine, N-myristoylglycine, methyl ester of N-myristoylglycine, ethyl ester of N-myristoylglycine, butyl ester of N-myristoylglycine, N-palmitoylglycine, N-stearoylglycine, octyl ester of N-stearoylglycine, stearyl ester of N-stearoylglycine, ethyl ester of N-dodecanoylalanine, ethyl ester of N-dodecanoylvaline, ethyl ester of N-dodecanoylleucine, ethyl ester of N-dodecanoylisoleucine and the like.

The derivatives of the amino acids having the formula [1] can be prepared by various conventional methods.

An acyl group having 1 to 20 carbon atoms can be introduced as the substituent $R^1$ of the amino group in the amino acid, for example, by the reaction of the amino acid with an acid halide having the desired number of carbon atoms. In this method, the amino group can be modified with the acyl group having 1 to 20 carbon atoms by dissolving the amino acid to be modified in an aqueous solution containing a scavenger of a hydrogen halide like sodium hydroxide, then adding an aqueous solution of a carboxylic acid halide having 1 to 20 carbon atoms and an aqueous solution containing the scavenger of the hydrogen halide to the above solution and allowing the reaction to proceed.

A hydrocarbon group having 1 to 20 carbon atoms can be introduced as the substituent $R^1$ of the amino group in the amino acid, for example, by the reaction of the amino acid with an alkyl ester of p-toluenesulfonic acid having the desired number of carbon atoms. A hydrocarbon group having 1 to 20 carbon atoms can be introduced as the substituent $R^2$ of carboxylic group in the amino acid, for example, by dropping thionyl chloride into an alcohol having the desired number of carbon atoms, then adding an amino acid or an amino acid having a substituent $R^1$ described above to the solution and then allowing the reaction to proceed.

The percutaneous absorption promoter is utilized in combination with pharmacologically active substances and applied to a patient percutaneously and locally. The kind of the pharmacologically active substance is not particularly limited but suitable substances can be selected and utilized from the generally known pharmacologically active substances.

Examples of the pharmacologically active substance are: steroid anti-inflammatory drugs, such as prednisolone, dexamethasone, hydrocortisone, fluocinolone acetonide, betamethasone varelate; betamethasone dipropionate and the like; non-steroid anti-inflammatory drugs, such as indomethacin, diclofenac, ibufenac, ibuprofen, ketoprofen, flufenamic acid, mefenamic acid, phenylbutazone, methyl salicylate and the like; antihistamic drugs, such as diphenhydramine, chmorpheniramine, promethazine, tripelenamine and the like; central nervous system acting drugs, such as chlorpromazine, nitrazepam, diazepam, phenobarbital, reserpine and the like; hormones, such as insuline, testosterone, methyltestosterone, progesterone, estradiol and the like; antihypertensive drugs, such as clonidine, reserpine, guanethidine sulfate and the like; cardiotonics, such as digitoxin, digoxine and the like; antiarrhythmic drugs, such as propranolol hydrochloride, procainamide hydrochloride, ajmaline, pindolol and the like; coronary vaso dilators, such as nitroglycerin, isosorbide dinitrate, erythritose tetranitrate, papaverine hydrochloride, nifedipine and the like; local anesthetics, such as lidocaine, benzocaine, procaine hydrochloride and the like; hypnotics and sedatives, such as barbital, thiopental, phenobarbital, cyclobarbital and the like; analgesics, such as morphine, aspirin, codeine, acetanilide, aminopyrine and the like; antibiotics, such as pencillin, tetracycline, erythromycin, streptomycin, gentamicin and the like; fungicides, such as benzalkonium chloride, acetophenylamine, nitrofurazone, pentamycin, naphthiomate and the like; anticancer drugs, such as 5-fluorouracil, busulfan, actinomycin, bleomycin, mitomycin and the like; diuretics, such as hydrochlorothiazide, penflutide, reserpine and the like; parasympatholytic drugs, such as scopolamine, atropine and the like; antiepileptics, such as nitrazepam, meprobamate and the like; antiparkinsonism drugs, such as chlorzoxazone, levodopa and the like; sulfa drugs, such as sulfamine, sulfamonomethoxine, sulfamethizole and the like, vitamins; prostaglandins; antipasm drugs; contraceptives and the like. Acidic pharmacologically active substances are preferable and acidic pharmacologically acidic substances having a carboxylic group are more preferable.

Examples of the acidic pharmacologically active substance having a carboxylic group are ibuprofen, flurbiprofen, phenoprofen, diclofenac, ibufenac, mefenamic acid, flufenamic acid, salycilic acid, acetylsalycilic acid and the like. Examples of the acidic pharmacologically active substance having no carboxylic group are: phenylbutazone, ketophenylbutazone, oxyphenbutazone, phenobarbital, amobarbital, cyclobarbital and the like.

The pharmacologically active substance can be used singly or as a combination of two or more kinds.

The percutaneous absorption promoter of the invention may be, according to desire, utilized in combination with various kinds of pharmacologically allowable additives, such as stabilizers, anti-aging agents, antioxidants, perfumes, fillers and other kinds of percutaneous absorption promoters.

The method of utilizing the percutaneous absorption promoter is not particularly limited. The promoter can be utilized in any form of conventionally utilized external preparations, such as ointments, creams, gels, lotions, liquids, sprays, cataplasmas, tape plasters and the like. The preferable form is tape plasters.

As the base of ointments and creams, fatty oils, lanolin, vaselin, paraffines, plastibases, glycols, higher fatty acids, higher alcohols and the like are utilized. If necessary, stabilizers, preservatives, emulsifiers, dispersants and the like may be added to the base. As the base of lotions, ethanol, glycerol, glycols and the like are utilized. As the base of liquids, ethanol, purified water, glycols and the like are utilized.

Examples of the base of cataplasmas are natural polymers, such as gelatin, sodium alginate, corn starch, traganth gum, casein and the like; celluloses, such as methyl cellulose, ethyl cellulose, hydroxyethyl cellulose, carboxymethyl cellulose and the like; starches, such as dextran, carboxymethyl starch and the like; and synthetic polymers, such as polyvinyl alcohol, sodium polyacrylate, polyvinyl pyrrolidone, polyvinyl ether and the like. If necessary, moisturing agents, such as glycerol, propylene glycol and the like, inorganic fillers, such as kaolin, bentonite, zinc oxide and the like, thickness adjusting agents, pH adjusting agents and the like may be compounded to the base.

As the adhesive for tapes and patches, for example, acrylic adhesives, rubber adhesives, silicone adhesives and the like are utilized.

The adhesives can be made into microreservoir-type materials by dispersing the pharmacologically active substance or a mixture of the pharmacologically active substance and a water soluble polymer within the adhesives. Dispersion of adhesives containing the pharmacologically active substance within the base of cataplasma can also be utilized.

The acrylic adhesives comprise, as the main component thereof, at least one polymer selected from the group consisting of, for example, homopolymers of acrylic esters, copolymers comprising two or more kinds of acrylic ester units and copolymers of acrylic esters and other functional monomers.

Examples of the acrylic ester are butyl (meth)acrylate, pentyl (meth)acrylate, hexyl (meth)acrylate, heptyl (meth) acrylate, octyl (meth)acrylate, nonyl (meth)acrylate, decyl (meth)acrylate and the like. Examples of the functional monomer are monomers containing a hydroxyl group, such as hydroxyethyl (meth)acrylate, hydroxypropyl (meth) acrylate and the like, and monomers containing an amide group, such as (meth)acrylamide, dimethyl (meth) acrylamide and the like.

The acrylic adhesives can be generally divided into solvent type adhesives and emulsion type adhesives. The solvent type adhesives generally comprise the acrylic polymer, solvents, crosslinking agents, adhesion promoters if desired and other ingredients. As the crosslinking system, the methylol group crosslinking system, the ionic crosslinking system, the urethane crosslinking system, the epoxy crosslinking system or the like are utilized.

The emulsion type adhesives generally comprise the acrylic polymer, emulsifiers, aqueous solvents, adhesion promoters if desired and other ingredients.

The rubber adhesives comprise, as the main components thereof, at least one polymer selected from the group consisting of, for example, natural rubber, polyisoprene rubber, polyisobutylene rubber, styrene-butadiene-styrene block copolymer and styrene-isoprene-styrene block copolymer.

Adhesion promoters, plasticizers, antioxidants, fillers and the like may be compounded with the rubber adhesives, if desired. The solvent type adhesives and the emulsion type adhesives using rubber latices are preferably utilized.

The silicone adhesives comprise, as the main components thereof, polydimethylsiloxane, polydiphenylsiloxane and the like. The solvent type adhesives comprising adhesive promoters, plastisizers, filler and the like are preferably utilized.

The adhesion promoters compounded with the adhesives according to the desire are, for example, natural resins, such as rosin resins, polyterpene resins and the like, petroleum resins such as $C_5$ resins, $C_9$ resins, DCPD resins and the like and synthetic resins, such as coumarone-indene resins, xylene resins and the like.

The base utilized for the tape plasters are, for example, sheets and films of synthetic resins, such as polyester, polyvinyl chloride, polypropylene, polyethylene, polyurethane and the like, synthetic papers, sheets and films of cellulose, nonwoven fabrics, woven fabrics, knitted fabrics and the like.

The amount of application of the percutaneous absorption promoter of the invention can be suitably selected according to the mode and the condition of the application. It is generally in the range from 0.1 to 50 weight %, preferably in the range from 0.5 to 30 weight % based on the total amount of the transdermal therapeutic formulation comprising the percutaneous absorption promoter. When the percutaneous absorption promoter is utilized in tape plasters, the amount is in the range from 5 to 30 weight % on the same basis.

The amount of the pharmacologically active substance is preferably in the range from 0.5 to 20 weight %, more preferably in the range from 1 to 10 weight %, based on the total amount of the transdermal therapeutic formulation.

It is the general understanding that the barrier property of skin against foreign substances is based on the structure of stratum corneum. This is more easily understood when one observes remarkably increased penetration of pharmacologically active substances through skin when the surface of the skin is partially removed by some cause, for example by cleavage of tape attached to the skin. The stratum corneum of skin is composed of layers of keratin cells which are made of proteins of flattened structures. It is generally understood that there are two main routes of passage for pharmacologically active substances: the transcellular route which is the passage through cells and the intercellular route which is the passage through interstices between cells. The stratum corneum cells are composed of keratin and lipids and, at the intercellular route, lamella layers are formed by amphiphillic materials such as phospholipids and the like, thus hydrophillic layers and lipophillic layer being accumulated to form a multilayer area. In the hydrophillic layers, molecules of water aggregate together to form clusters. Both of the hydrophillic and lipophillic layers show high resistance against diffusion of foreign substances and it is generally understood that the barrier property of skin is caused by the tight structure of the skin layers as described here.

The derivatives of amino acids having the formula |1| have particularly high affinity to lipids and give fluctuations to the lipids, this condition is believed to cause decrease of the resistance against diffusion and increase of the permeation of the pharmacologically active substances. The derivatives of amino acids are considered to affect the structure of water molecules by the effect on the lipids and, thus, to cause increase of the permeation of the substances.

The percutaneous absorption promoter of the invention is a derivative of amino acids having the same backbone structure as that of the amino acids showing the function of vitamin L1, one of the vitamins found in the body. It is therefore decomposed to compounds harmless to the body by enzymes in the body, such as esterase, peptidase and the like.

DESCRIPTION OF THE PREFERRED EMBODIMENTS

The invention will be understood more readily with reference to the following examples; however, these examples are intended to illustrate the invention and are not to be construed to limit the scope of the invention.

Example of preparation of derivatives of anthranilic acid

Example of preparation of material 1

Synthesis of N-n-octanoylanthranilic acid

Anthranilic acid was dissolved in a mixed solvent containing pyridine and tetrahydrofuran (THF) in 5:5 ratio and a THF solution of n-caprioyl chloride was dropped to the solution during several hours for reaction. After the reaction, hydrochloric acid was added to the reaction mixture. Pyridine hydrochloride was filtered and the solvent was removed. N-n-octanoylanthranilic acid was obtained from the remaining reactant after the purification by column chromatography with the yield of 79.4%.

Example of preparation of material 2

Synthesis of N-n-octylanthranilic acid

To a solution of anthranilic acid in toluene, n-octyl p-toluenesulfonate prepared according to the conventional method was added and the mixture was refluxed at 120° C. After 6 hours, an aqueous solution of sodium hydroxide was added and the toluene layer was concentrated. N-n-octylanthranilic acid was obtained from the remaining reactant after the purification by column chromatography with the yield of 43.1%.

Example of preparation of material 3

Synthesis of ethyl N-n-octanoylanthranilate

Thionyl chloride was dropped to ethanol and the mixture was stirred for 2 hours. Then, N-n-octanoylanthranilic acid was added to the mixture and reaction was allowed to proceed for 3 days at the room temperature. After the reaction, the solvent was removed and ethyl N-n-octanoylanthranilate was obtained from the remaining reactant after the purification by column chromatography with the yield of 89.2%.

Various kinds of derivatives of anthranilic acid shown in Table 1 were prepared by the similar methods to the above.

Example of preparation of derivatives of glycine

Example of preparation of material 4

To a solution of glycine in a 1 N-sodium hydroxide, an ether solution of n-dodecanoyl chloride and a 1 N-aqueous solution of sodium hydroxide were dropped simultaneously and the mixture was stirred for 1 hour. The reaction mixture was then neutralized with hydrochloric acid and ether was removed from the solution. N-n-dodecanoylglycine was obtained from the remaining reactant after the purification by column chromatography with the yield of 84.7%. The melting point of the product was 115.5° to 116.7° C.

Various kinds of derivatives of glycine having the amino group modified with an acyl group as shown in Table 2 were prepared by the similar methods to the above.

Example of preparation of material 5

Thionyl chloride was dropped to ethanol and the mixture was stirred for 1 hour. Then, N-n-dodecanoylglycine was added to the mixture and reaction was allowed to proceed for 2 days at the room temperature. After the reaction, the solvent was removed and ethyl ester of N-n-dodecanoylglycine was obtained from the remaining reactant after the purification by column chromatography with the yield of 94.1%. The melting point of the product was 42.1° to 43.2° C.

Various kinds of derivatives of glycine having the amino group modified with an acyl group and the carboxylic group modified with an alkyl group as shown in Table 2 were prepared by the similar methods to the above.

Example of preparation of material 6

Derivatives of glycine having the carboxylic group modified with an alkyl group as shown in Table 2 were prepared by the same method as in Example of preparation of material 5 except that glycine was used in place of the derivative of glycine having the amino group modified with the acyl group.

Example of preparation of material 7

Derivatives of various amino acids having the carboxylic group modified with an alkyl group were prepared by the same method as in Example of preparation of material 5 except that the derivative of glycine having the amino group modified with the acyl group was replaced by one of the following compounds: N-n-dodecanoyl-L-alanine, N-n-dodecanoyl-L-valine, N-n-dodecanoyl-L-leucin and N-n-dodecanoyl-L-isoleusine.

Example of preparation of material 8

Glycine was dissolved in a 2:1 mixture by volume of IPA and water. Triethylamine and 1-bromododecane were added to the solution successively and the mixture was kept stirring for more than 7 days. After the solvent was removed, THF was added to the remaining material. Triethylamine hydrobromide was removed by filtration and the filtrate was concentrated. N-n-dodecylglycine was obtained from the concentrated solution by separation and purification by column chromatography with the yield of 26.3%.

N-n-decylglycine was prepared by the same method as above.

The acyl groups and the carboxyl groups used for modifying the amino group in Examples of preparation of material 1 to 8 were normal isomers in all cases.

EXAMPLE 1

Percutaneous permeability test

In a vertical Franz type cell, a piece of skin taken from abdomen of a Wister rat was used as the permeation membrane. As the donor solution, a solution of indomethacin as the model pharmacologically active substance and a derivative of anthranilic acid (1 weight %, respectively) in a 50% aqueous solution of ethanol was used. As the receiver solution of the permeation, a buffer solution of phosphoric acid of pH 7.2 was used. Concentration of the pharmacologically active substance in the receiver solution was measured with time by high performance liquid chromatography (HPLC).

Ratio of the peak areas of the pharmacologically active substance and the internal standard substance was obtained from the HPLC chart. The concentration of the pharmacologically active substance was obtained by using the calibration curve which had been made beforehand. (The method of internal standard)

Table 1 shows the value of the accumulated permeation of every derivative of anthranilic acid based on the value of the control run. The value was obtained as the ratio of the concentrations of the pharmacologically active substance in the presence and in the absence of a derivative of anthranilic acid after the permeation of 24 hours.

TABLE 1

| derivative or anthranilic acid | permeation based on the control |
|---|---|
| anthranilic acid | 1.86 |
| N-acetylanthranilic acid | 1.94 |
| N-n-octanoylanthranilic acid | 2.46 |
| N-n-dodecanoylanthranilic acid | 2.28 |
| N-n-octadecanoylanthranilic acid | 2.14 |
| ethyl N-acetylanthranilate | 2.04 |
| n-butyl N-acetylanthranilate | 3.69 |
| ethyl N-n-octanoylanthranilate | 4.29 |
| n-butyl N-n-octanoylanthranilate | 3.46 |
| lauryl N-n-octanoylanthranilate | 3.16 |
| methyl N-n-dodecanoylanthranilate | 2.43 |
| ethyl N-n-dodecanoylanthranilate | 4.00 |
| n-butyl N-n-dodecanoylanthranilate | 2.63 |
| ethyl N-n-octadecanoylanthranilate | 2.41 |
| n-butyl N-n-dodecanoylanthranilate | 2.33 |
| lauryl N-n-octadecanoylanthranilate | 2.10 |
| stearyl N-n-octadecanoylanthranilate | 1.89 |
| stearyl N-n-octanoylanthranilate | 2.01 |
| methyl anthranilate | 2.36 |
| ethyl anthranilate | 2.60 |
| n-butyl anthranilate | 4.14 |
| n-octyl anthranilate | 3.97 |
| lauryl anthranilate | 3.81 |
| stearyl anthranilate | 2.10 |
| N-n-octylanthranilic acid | 2.05 |
| ethyl N-n-octylanthranilate | 2.45 |

EXAMPLE 2

Activity of promoting the percutaneous absorption was evaluated on the derivatives of the amino acids prepared in Examples of preparation of material 4 to 6 by using indomethacin as the pharmacologically active substance. Results of the evaluation are shown in Table 2.

TABLE 2

| derivative of glycin | permeation based on the control |
|---|---|
| N-n-butanoylglycin | 1.25 |
| N-n-octanoylglycine | 1.38 |
| N-n-decanoylglycine | 1.43 |
| N-n-dodecanoylglycine | 2.85 |
| N-n-tetradecanoylglycine | 2.25 |
| N-n-hexadecanoylglycine | 3.81 |
| N-n-octadecanoylglycine | 1.34 |
| ethyl ester of N-n-butanoylglycine | 2.01 |
| n-octyl ester of N-n-butanoylglycine | 3.37 |
| stearyl ester of N-n-butanoylglycine | 1.24 |
| methyl ester of N-n-dodecanoylglycine | 3.87 |
| ethyl ester of N-n-dodecanoylglycine | 5.19 |
| n-butyl ester of N-n-dodecanoylglycine | 4.97 |
| n-octyl ester of N-n-dodecanoylglycine | 2.61 |
| n-stearyl ester of N-n-dodecanoylglycine | 1.23 |
| methyl ester of N-n-tetradecanoylglycine | 4.73 |
| ethyl ester of N-n-tetradecanoylglycine | 2.82 |
| n-butyl ester of N-n-tetradecanoylglycine | 4.04 |
| n-octyl ester of N-n-octadecanoylglycine | 1.20 |
| n-stearyl ester of N-n-octadecanoylglycine | 1.16 |
| ethyl ester of glycine | 1.22 |
| n-octyl ester of glycine | 1.47 |
| stearyl ester of glycine | 1.30 |

The activity of promoting the percutaneous absorption of the pharmacologically active substances by the percutaneous absorption promoter of the invention can be examined, for example, by the in vitro diffusion test using a piece of skin taken from abdomen of a rat. When indomethacin was used as the pharmacologically active substance, the activities of promoting the percutaneous absorption of the pharmacologically active substance by the percutaneous absorption promoters were found to be 5.19, 4.97, 4.73 and 4.04 for ethyl ester of N-n-dodecanoylglycin, n-butyl ester of N-n-dodecanoylglycin, methyl ester of N-myristoylglycine and n-butyl ester of N-myristoylglycine, respectively, based on the activity of the control. Thus it was found that the formulations using the percutaneous absorption promoters of the invention have activities more than four times higher than the formulation without them.

EXAMPLE 3

Activity of promoting the percutaneous absorption of ethyl N-n-octanoylanthranilate prepared in Example of preparation of material 3 was-evaluated by using indometbacin, sodium salycilate or ketoprofen, predonisolone and pindolol as the pharmacologically active substance according to the same method as in Example 1. Results of the evaluation are shown in Table 3. The values shown were measured after 24 hours and expressed as the value based on the control.

TABLE 3

| pharmacologically active substance | result based on control |
|---|---|
| indomethacin | 4.29 |
| sodium salycilate | 1.37 |
| ketoprofen | 3.25 |
| predonisolone | 5.86 |
| pindolol | 9.88 |

EXAMPLE

Activities of promoting the percutaneous absorption of the derivatives of amino acids prepared in Example of preparation of material 7 were evaluated by using indomethacin as the pharmacologically active substance. Results are shown in Table 4.

TABLE 4

| derivative of amino acid | result based on control |
|---|---|
| ethyl ester of N-n-dodecanoyl-L-alanine | 2.57 |
| ethyl ester of N-n-dodecanoyl-L-valine | 2.16 |
| ethyl ester of N-n-dodecanoyl-L-leucin | 1.89 |
| ethyl ester of N-n-dodecanoyl-L-isoleucin | 2.44 |

EXAMPLE 5

Activities of promoting the percutaneous absorption of the derivatives of N-n-decylglycine and N-n-dodecylglycine prepared in Example of preparation of material 8 were evaluated by using indomethacin as the pharmacologically active substance. Results are shown in Table 5.

TABLE 5

| derivative of amino acid | result based on control |
|---|---|
| ethyl ester of N-n-decylglycine | 3.88 |
| ethyl ester of N-n-dodecylglycine | 1.52 |

EXAMPLE 6

Activity of promoting the percutaneous absorption of ethyl ester of N-n-dodecanoylglycine prepared in Example of preparation of material 5 was evaluated by using indomethacin, sodium salicylate, ketoprofen, predonisolone and pindolol as the pharmacologically active substance.

Results were 5.19, 4.27, 1.52, 5.01 and 19.13 for indomethacin, sodium salicylate, ketoprofen, predonislone and pindolol, respectively, based on the value of control.

EXAMPLE 7

Preparation of tape plaster comprising derivatives of anthranilic acid n-Butyl acrylate was dissolved in ethyl acetate to form a 40 weight % solution and 0.4 mol % of azoisobutyronitrile was added to the solution as the initiator. The reaction mixture was allowed to polymerize under nitrogen stream at 70° C. for 8 hours. Into the polymer solution thus prepared, 20 weight parts of indomethacin and 20 weight parts of ethyl Non-octanoylanthranilate based on 100 weight parts of the solid polymer were dissolved. The solution was cast on a polyester film and dried at 100° C. for I minute to form an adhesive layer of 30 μm. A polyester film which had been treated with release coating was attached to the adhesive layer to prepare the tape plaster.

Percutaneous permeability test

In a vertical Franz type cell, a piece of skin taken from abdomen of a hairless rat was used as the permeation membrane. The tape plaster prepared above was applied to the skin. As the receiver solution of permeation, a buffer solution of phosphoric acid of pH 7.2 was used. Concentration of the pharmacologically active substance in the receiver solution was measured with time by high performance liquid chromatography (HPLC). Results are shown in Table 7.

TABLE 7

| | permeation of the active substance $\mu g/cm^2 \cdot 24$ hr | value based on the control |
|---|---|---|
| Comparative example as the control | 85 | — |
| Example containing the promoter | 330 | 3.88 |

In Table 7, ethyl N-n-octanoylanthranilate was not used in Comparative example while it was used in Example.

Irritation test to skin

Irritation test to skin was made on 10 male persons of the age of 25 to 30. A tape plaster containing the derivative of anthranilic acid prepared above was applied to the inside of an upper arm and condition of the skin was examined by visual observation. Results are shown in Table 8. The results are expressed in terms of the following notations.

++: remarkable erythema or edema

+: erythema or edema

−: no change

TABLE 8

| test number (person) | tape plaster containing the promoter | control |
|---|---|---|
| 1 | − | − |
| 2 | − | + |
| 3 | − | − |
| 4 | − | − |
| 5 | − | − |
| 6 | − | − |

TABLE 8-continued

| test number (person) | tape plaster containing the promoter | control |
|---|---|---|
| 7 | + | + |
| 8 | − | − |
| 9 | − | − |
| 10 | + | − |

The results in Table 8 show that the permeation of indomethacin was promoted and the lag time was decreased.

While the invention has been particularly shown and described with reference to preferred embodiments thereof, it will be understood by those skilled in the art that the foregoing and other changes in form and details can be made therein without departing from the spirit and scope of the invention.

To summarize the advantages obtained by the invention, the percutaneous promoter of the invention has excellent ability of promoting the percutaneous absorption of the pharmacologically active substances and excellent safety simultaneously, capable of delivering the desired pharmacologically active substances rapidly to the location of treatment or to all parts of the body through the circulating system and effective for curing various kinds of disease. The tape plaster comprising it and the method of promoting percutaneous absorption by utilizing it have the same advantages.

What is claimed is:

1. A percutaneous absorption promoter composition which comprises (a) a pharmaceutically active substance and (b) a derivative of amino acid having the formula:

$$R^1NH—R^3—COOR^2$$

wherein $R^1$ is an acyl group having 1 to 20 carbon atoms, $R^2$ is a hydrogen atom or a hydrocarbon group having 1 to 4 carbon atoms and $R^3$ is

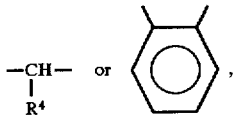

$R^4$ being a hydrogen atom, methyl group, isopropyl group, 2-methylpropyl group or 1-methylpropyl group.

2. A percutaneous absorption promoter as claimed in claim 1 wherein $R^1$ is a saturated or unsaturated aliphatic acyl group having 1 to 20 carbon atoms and $R^2$ is a saturated or unsaturated aliphatic hydrocarbon group having 1 to 4 carbon atoms.

3. A percutaneous absorption promoter as claimed in claim 1 wherein $R^1$ is a saturated or unsaturated linear aliphatic acyl group having 2 to 16 carbon atoms and $R^2$ is a saturated or unsaturated aliphatic hydrocarbon group having 1 to 4 carbon atoms.

4. A percutaneous absorption promoter as claimed in claim 1 wherein $R^4$ is a hydrogen atom.

5. A tape plaster comprising a percutaneous absorption promoter composition as claimed in claim 1 said tape plaster comprising an adhesive material containing the amino acid derivative and at least one pharmacologically active substance coated on a tape substrate.

6. A tape plaster as claimed in claim 5 wherein $R^1$ is a saturated or unsaturated aliphatic acyl group having 1 to 20 carbon atoms and $R^2$ is a saturated or unsaturated aliphatic hydrocarbon group having 1 to 4 carbon atoms.

7. A tape plaster as claimed in claim 5 wherein $R^1$ is a saturated or unsaturated linear aliphatic acyl group having 2 to 16 carbon atoms and $R^2$ is a saturated or unsaturated aliphatic hydrocarbon group having 1 to 4 carbon atoms.

8. A tape plaster as claimed in claim 5 wherein $R^4$ is a hydrogen atom.

9. A tape plaster as claimed in claim 5 wherein the pharmacologically active substance is selected from the group consisting of indomethacin, ketoprofen, predonisolone and pindolol.

10. A tape plaster as claimed in claim 5 wherein the pharmacologically active substance is selected from the group consisting of indomethacin, predonisolone and pindolol.

11. A method of promoting percutaneous absorption which comprises promoting percutaneous absorption of a pharmacologically active substance by applying a percutaneous absorption promoter in combination with the pharmacologically active substance to a patient topically and percutaneously, the percutaneous absorption promoter comprising a derivative of amino acid having the formula:

$$R^1NH—R^3—COOR^2$$

wherein $R^1$ is an acyl group having 1 to 20 carbon atoms, $R_2$ is hydrocarbon group having 1 to 4 carbon atoms and $R^3$ is

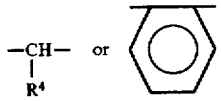

$R^4$ being a hydrogen atom, methyl group, isopropyl group, 2-methylpropyl group or 1-methylpropyl group.

12. A method of promoting percutaneous absorption as claimed in claim 11 wherein $R^1$ is a saturated or unsaturated aliphatic acyl group having [1] 1 to 20 carbon atoms and $R^2$ is a saturated or unsaturated aliphatic hydrocarbon group having 1 to 4 carbon atoms.

13. A method of promoting percutaneous absorption as claimed in claim 11 wherein $R^1$ is a saturated or unsaturated linear aliphatic acyl group having 2 to 16 carbon atoms and $R^2$ is a saturated or unsaturated aliphatic hydrocarbon group having 1 to 4 carbon atoms.

14. A method of promoting percutaneous absorption as claimed in claim 11 wherein $R^4$ is a hydrogen atom.

15. A method of promoting percutaneous absorption as claimed in claim 11 wherein the pharmacologically active substance is selected from the group consisting of indomethacin, ketoprofen, predonisolone and pindolol.

16. A method of promoting percutaneous absorption as claimed in claim 11 wherein the pharmacologically active substance is selected from the group consisting of indomethacin, predonisolone and pindolol.

17. A percutaneous absorption promoter composition as claimed in claim 1 which further comprises an adhesive effective to cause the composition to adhere to skin to which it is applied.

18. The percutaneous absorption promoter of claim 1, where $R^3$ is

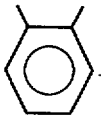

19. The tape plaster of claim 5, wherein $R^3$ is

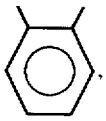

20. The method of promoting percutaneous absorption of claim 11, wherein $R^3$ is

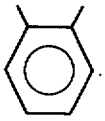

21. A percutaneous absorption promoter composition which comprises (a) a pharmaceutically active substance and (b) a derivative of an amino acid having the formula:

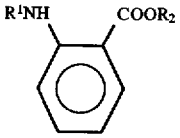

wherein $R^1$ is *a hydrogen atom*, an acyl group having 1 to 20 carbon atoms, *or a hydrocarbon group having 1 to 20 carbon atoms*, and $R^2$ is a hydrogen atom or a hydrocarbon group having 1 to 20 carbon atoms.

22. A method of promoting percutaneous absorption which comprises promoting percutaneous absorption of a pharmaceutically active substance by applying a percutaneous absorption promoter composition of claim 21 to a patient topically and percutaneously.

* * * * *